(12) United States Patent
Zappala' et al.

(10) Patent No.: US 6,740,741 B2
(45) Date of Patent: May 25, 2004

(54) DIAZO DERIVATIVES AND PROCESS FOR THEIR PREPARATION

(75) Inventors: Antonio Zappala', Rome (IT); Andrea Gorassini, Udine (IT); Angelo Guimanini, deceased, late of Udine (IT); by Eva Gacs, legal representative, Tavagnacco (IT); Giancarlo Verardo, Pordenone (IT)

(73) Assignees: Consiglio Nazionale delle Ricerche, Rome (IT); Universita'degli Studi di Udine, Udine (IT)

( * ) Notice: Subject to any disclaimer, the term of this patent is extended or adjusted under 35 U.S.C. 154(b) by 0 days.

(21) Appl. No.: 10/189,695

(22) Filed: Jul. 3, 2002

(65) Prior Publication Data

US 2003/0065153 A1 Apr. 3, 2003

(30) Foreign Application Priority Data

Jul. 4, 2001 (IT) .................. MI2001A001412

(51) Int. Cl.⁷ .................. C07C 245/14; C07C 271/20; C07C 281/02; C07D 295/13; D21H 25/18
(52) U.S. Cl. .................. 534/560; 534/558; 534/565; 546/247; 544/168; 560/159; 162/160; 422/40
(58) Field of Search .................. 534/558, 560, 534/565; 546/247; 162/160; 422/40; 544/168; 560/159

(56) References Cited

U.S. PATENT DOCUMENTS 3,163,536 A * 12/1964 Nishio et al. .................. 430/599
3,513,241 A * 5/1970 Hoyer et al. .................. 514/478

FOREIGN PATENT DOCUMENTS

| DE | 1155328 | 3/1963 | |
| DE | 2313012 | * 10/1974 | |
| DE | 2528496 | * 1/1976 | |
| EP | 0545180 | 9/1993 | .......... D21H/25/18 |
| EP | 1273707 | 8/2003 | .......... D21H/25/18 |
| WO | WO-97/29097 | * 8/1979 | |

OTHER PUBLICATIONS

Pecher et al., Chemical Abstracts, 53:3088, 1959.*
Rav–Acha et al., Chemical Abstracts, 111:96377, 1989.*
Ch. Rav–Acha, "The Catalytic Effect of Cationic Amino Micelles on the Hydrolysis of Substituted Phenyl Esters", *Tetrahedron*, vol. 44, No. 18, pp. 5879 to 5892, (1988).
Pecher et al., "Aminoethylurees, Aminoethylthiourees ET Aminoethylurethannes Substitues, Et Leur Action Sur La Filariose", *Bull Soc. Chim. Belg*, 66, pp. 545–564, (1957).
Buckley et al., "Decomposition of Aliphatic Diazo–Compounds, by Trimethyl Borate: *The Preparation of* Branched–Chain Paraffins of High Molecular Weight", *Chemical Society*, pp. 3701–3704 (1952).
Abstract of South African Patent 6706747, Nov. 8, 1968.

* cited by examiner

*Primary Examiner*—Fiona T. Powers
(74) *Attorney, Agent, or Firm*—Abelman, Frayne & Schwab

(57) ABSTRACT

Novel diazo derivatives useful for the deacidification of paper material and the process for their preparation comprising three steps starting from an amine and ethyl chlorocarbonate, are described.

14 Claims, No Drawings

DIAZO DERIVATIVES AND PROCESS FOR THEIR PREPARATION

FIELD OF THE INVENTION

The present invention concerns novel diazo derivatives of general formula (I) hereafter reported, the process for their preparation and their use as deacidifying agents in the deacidification treatment of paper.

STATE OF THE ART

It is universally acknowledged that one of the causes of the too rapid deterioration of cultural materials on paper is the presence of acidity in the material. p In modern paper, acidity is usually caused during the manufacture in the paper factory; however, acidity can often be found even in papers or books that are made from acid-free paper, as it comes from some types of ink for manuscripts, that was widely used in the past.

Experts agree that in order to prolong the life of books and documents that are stored in libraries and archives (according to the experts from three to five times as much) it is necessary to eliminate the acidity from the materials, by using a technique that in the specialised environment is known as "deacidification". Obviously, in order to avoid the errors committed in the past, new documents and books to be stored should be made with acid-free paper (UNI n. 10332—Paper for documents. Requirements for the maximum duration and durability and UNI n. 10333—Paper for documents. Requirements for duration).

In the Italian public libraries there are currently 30 million books; an equal amount of paper documents are kept in public archives.

From fragmentary surveys carried out in some Italian preservation environments, in agreement with similar research carried out abroad on a wider scale, it has been found that 20–30% of library and archive materials are now so fragile that they cannot be made available for free consultation; the risk of further damage would be too high. Alongside this relatively low percentage however, it has been found that 60–80% of preserved books and documents need to be deacidified or in some way stabilised; otherwise, it would only be a matter of time before all the acid material would become fragile, and no longer consultable.

In view of what above said, it is evident that, in order to protect the Italian book and document heritage, it is necessary to be able to intervene with mass deacidification techniques, or however, with stabilisation techniques that would slow down deterioration; these would be techniques that allow the entire heritage to be restored in a time span of no more than ten, fifteen years.

It is therefore much felt the need for products that allow effective and persistent deacidification of paper, without secondary effects on the material treated.

SUMMARY

The Applicant has now found novel diazo derivatives of general formula (I) that are effective as deacidifying agents in the deacidification treatment of paper, without showing the drawbacks of the deacidification methods that have been used so far, and a process for their preparation.

Therefore subject of the present invention are the diazo derivatives of general formula (I)

wherein R' is chosen from H and methyl, and R is the group

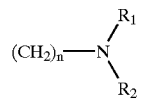

where n=1, 2, 3, 4, 5; and $R_1$ and $R_2$, equal to one another, are chosen between methyl and ethyl, or $R_1$ and $R_2$, taken together, form with N a piperidine ring or a 4-morpholine ring;

provided that, when n=2 and R'=H, $R_1$ and $R_2$ are different from methyl.

Further subject of the invention is the process for the preparation of the diazo derivatives of general formula (I)

wherein R' is chosen from H and methyl, and R is the group

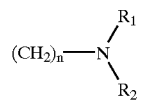

where n=1, 2, 3, 4, 5; and $R_1$ and $R_2$, equal to one another, are chosen between methyl and ethyl, or $R_1$ and $R_2$, taken together, form with N a piperidine ring or a 4-morpholine ring;

comprising the following steps:
a) reaction between the amine of formula (II) and ethyl chlorocarbonate of formula (III) to obtain carbamate (IV)

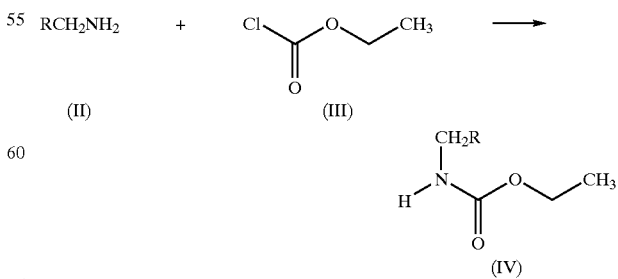

in which R is defined as above;

b) nitrosation of the carbamate (IV) obtained from the step a) to obtain N-nitroso-carbamate of formula (V):

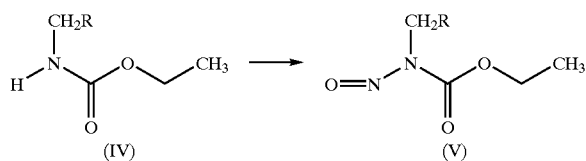

wherein R is defined as above;

c) reduction of the N-nitroso-carbamate (V) obtained from step b) to obtain the desired formula (I) compound:

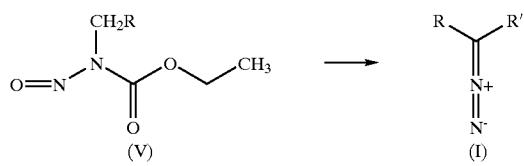

wherein R and R' are defined as above.

Further subjects of this invention are the formula (IV) compounds and their N-nitroso derivatives of formula (V); and the use of the formula (I) compounds in the deacidification methods of paper material.

DETAILED DESCRIPTION OF THE INVENTION

According to a particular embodiment of the present invention, step a) of the present process is carried out at room temperature using $CH_2Cl_2$ as a solvent, and with a large excess of $K_2CO_3$ so as to completely neutralise the HCl that forms during the reaction; the preferred stoichiometric ratio between amine (II), $K_2CO_3$ and ethyl chlorocarbonate (III) is 1:4:3.

The reaction in step b) of the present process can be carried out at a temperature of 1–2° C. using $HCl/NaNO_2$ as reagent. A large excess of $HCl/NaNO_2$ is preferably used so as to achieve complete nitrosation of the formula (IV) product.

According to a particular embodiment of the invention, step c) of the present process is carried out at a temperature of 1–2° C. with a solution of sodium methoxide in methanol. By using a slight excess of sodium methoxide compared to the amount of the formula (V) compound, the formula (I) compound is obtained in which R' is H, whereas with a large excess of sodium methoxide, the compound (I) is obtained in which R' is methyl. Methanol, ethanol and $Na_2CO_3$ are obtained as the only secondary reaction products.

The so obtained product is dissolved in a suitable inert stabilising solvent, preferably in diethyl ether, and the ether solution of the products is kept at a temperature of –18° C. and away from light, and it is used in this form without isolating the product.

The formula (I) compounds can be used for the deacidification of paper products according to techniques known in the art; preferably, these compounds can be used in mass deacidification techniques, where "mass deacidification techniques" means the technique described in the copending patent application in the name of the same Applicant, wherein an increase in the pH up to 9–10 of the paper material treated is obtained, and such an increase persists in time for at least 6 months. Following the treatment with compounds of general formula (I) prepared with the present process, no undesired side effects were noted, such as the formation of unpleasant odours or colouring caused by the treatment itself.

The present compound of formula (I) wherein R' is H and R is the group

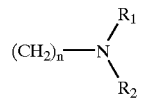

where n=1, and $R_1$ and $R_2$, taken together, from with N a piperidine ring, has proved to be especially effective in obtaining a prolonged continuation of the basic pH obtained by the deacidification treatment.

The following examples are given to provide non-limiting illustrations of the present invention.

EXAMPLE 1

Synthesis of the Compound (III) wherein R is (1-piperidine)methyl

In a flask containing 3.9 g of $K_2CO_3$ (MW=138.21, 28 mmol) 15 ml of $CH_2Cl_2$ are added; the mixture is maintained under strong stirring for 10 min. at 20–25° C., and then 1 ml of 1-(2-aminoetil)piperidine (MW=128.22, d=0.899, 0.9 g, 7 mmol) is added. The mixture is kept under strong stirring at 5–6° C. for 5 min. Then 2 ml of ethyl chlorocarbonate (MW=108.52, 21 mmol) are added dropwise and the mixture is kept under strong stirring at 20–25° C. After 90 minutes the mixture is filtered onto paper to remove the non reacted $K_2CO_3$ and is purified via crystallisation in diethyl ether.

1.1 g of a white solid are obtained, that by means of GC-MS and $^1H$-NMR analysis was found to be [2-(1-piperidine)ethyl]carbamate (MW=200.28, 5.5 mmol, yield=78%). The product is kept in the dark at 4° C.

EXAMPLE 2

Synthesis of the Compound (V) in which R is (1-piperidine)methyl

In a flask containing 2 ml of water, 1.7 ml of HCl 37% by weight (MW=36.46, 20 mmol) are added, and the temperature is brought up to 1–2° C. Under strong stirring, 1 g of [2-(1-piperidine)ethyl]ethylcarbamate (MW=200.28, 5 mmol) obtained as described in Example 1 is added, and 1 g of $NaNO_2$ (MW=69.00, 15 mmol) previously dissolved in 2 ml of water. Once the addition is completed, the reaction mixture is kept at the same temperature and under stirring for another 60 minutes, then the pH is brought to basic values by adding 15 ml of a saturated solution of $Na_2CO_3$, and the extraction with 40 ml of diethyl ether is carried out. Finally, the organic phase is dehydrated with anhydrous $Na_2SO_4$, then filtered onto paper, and the solvent is removed via distillation in a vacuum at 25° C. and away from the light.

0.73 g of a yellow-orange oil are thus obtained, which is identified via $^1H$-NMR and $^{13}C$-NMR as N-nitroso-[2-(1-piperidine)ethyl]ethylcarbamate (MW=229.28, 3 mmol, yield=64%). The product is kept at a temperature below –18° C. and away from the light.

EXAMPLE 3

Synthesis of the Compound (I) in which R is (1-piperidine)methyl 0.7 g of -N-nitroso-[2-(1-piperidine)ethyl]ethylcarbamate obtained as described in Example 2 are diluted with 5 ml of diethyl ether and added dropwise into a flask containing 0.2 g of sodium methoxide (MW=54.02, 4 mmol), 1 ml of diethyl ether and 1 ml of methanol; the reaction mixture is maintained under constant stirring and is kept at a temperature of 1–2° C.

Once the addition is completed, the mixture is diluted with additional 25 ml of diethyl ether, and the $Na_2CO_3$ is removed by decantation. An ether solution of the desired product 2-(1-piperidine)diazoethane (MW=139.21) is thus obtained, having a concentration of 3 mmol/30 ml, i.e. 0.1 M.

This solution is kept at a temperature of –18° C. and away from the light.

What is claimed is:

1. Diazo derivatives of general formula (I)

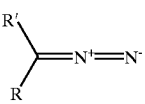

wherein R' is H, and R is the group

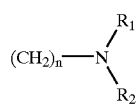

where n=1; and $R_1$ and $R_2$, taken together, form with N a piperidine ring.

2. Process for the preparation of diazo derivatives of general formula (I)

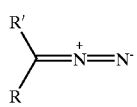

in which R' is chosen between H and methyl, and R is the group

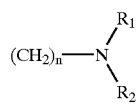

where n=1, 2, 3, 4, 5; and $R_1$ and $R_2$, equal to one another, are chosen between methyl and ethyl, or $R_1$ and $R_2$, taken together, form with N a piperidine ring or a 4-morpholine ring;

comprising the following steps:

a) reaction between the amine of formula (II) and ethyl chlorocarbonate of formula (III) to obtain the carbamate of formula (IV)

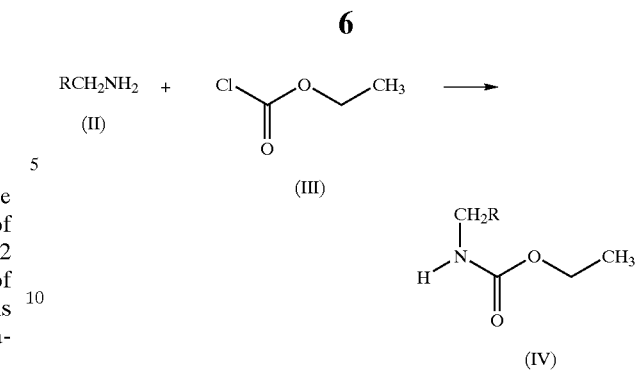

wherein R is as defined above;

b) nitrosation of the carbamate (IV) obtained from step a) to obtain the N-nitroso-carbamate of formula (V):

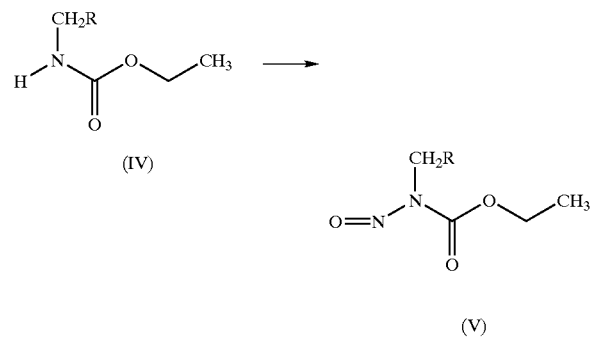

wherein R is as defined above;

c) reduction of the N-nitroso-carbamate (V) obtained from step b) to obtain the desired compound of formula (I):

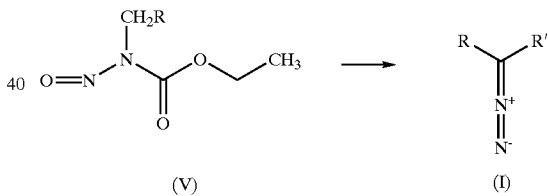

wherein R and R' are defined above.

3. The process according to claim 2, wherein the said reaction between the amine of formula (II) and ethyl chlorocarbonate of formula (III) in step a) is carried out in the presence of $K_2CO_3$, at room temperature and using $CH_2Cl_2$ as solvent.

4. The process according to claim 3, wherein the stoichiometric ratio between the amine of formula (II), $K_2CO_3$ and ethyl chlorocarbonate (III) in step a) is 1:4:3.

5. The process according to claim 2, wherein the said step b) is carried out using $HCl/NaNO_2$, at a temperature of 1–2° C.

6. The process according to claim 5, wherein said step b) is carried out with a strong excess of $HCl/NaNO_2$ compared to the carbamate of formula (IV).

7. The process according to claim 2, wherein said step c) is carried out using a methanol solution of sodium methoxide, at a temperature of 1–2° C.

8. The process according to claim 7, wherein, in order to obtain the formula (I) compound in which R' is H, said step c) is carried out using a slight excess of sodium methoxide compared to formula (V) compound.

9. The process according to claim 7, wherein, in order to obtain the formula (I) compound, in which R' is methyl said step c) is carried out using a large excess of sodium methoxide compared to formula (V) compound.

10. The process according to claim 2 for the preparation of formula (I) diazo derivative wherein R' is H and R is the group

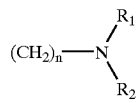

where n=1, and $R_1$ and $R_2$ together form with N a piperidine ring.

11. A process for the deacidification treatment of paper by applying thereto a diazo derivative of formula (I)

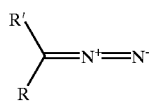 (I)

in which R' is selected from the group consisting of H and methyl, and R is the group

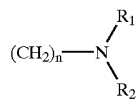

where n=1, 2, 3, 4 or 5; and $R_1$ and $R_2$ are equal to one another, are selected from the group consisting of methyl and ethyl, or $R_1$ and $R_2$, taken together, form with N a piperidine ring or a 4-morpholine ring.

12. The process according to claim 11, wherein said deacidification treatment is carried out using the mass deacidification technique.

13. The process according to claim 11, wherein in said diazo derivative of general formula (I) R' is H and R is the group

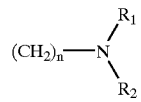

where n=1, and $R_1$ and $R_2$, taken together, form with N a piperidine ring.

14. N-nitroso compounds of formula (V)

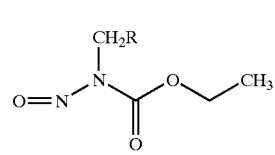 (V)

wherein R is the group

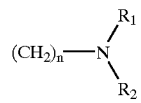

where n=1; and $R_1$ and $R_2$, taken together, form with N a piperidine ring.

* * * * *